(12) United States Patent
Khurana

(10) Patent No.: US 11,890,381 B2
(45) Date of Patent: Feb. 6, 2024

(54) NATURAL LUBRICANT COMPOSITION AND A TABLET

(71) Applicant: NITIKA PHARMACEUTICAL SPECIALITIES PVT. LTD., Maharashtra (IN)

(72) Inventor: Ravleen Singh Khurana, Maharashtra (IN)

(73) Assignee: NITIKA PHARMACEUTICAL SPECIALITIES PVT. LTD., Nagpur (IN)

( * ) Notice: Subject to any disclaimer, the term of this patent is extended or adjusted under 35 U.S.C. 154(b) by 129 days.

(21) Appl. No.: 17/468,717

(22) Filed: Sep. 8, 2021

(65) Prior Publication Data

US 2022/0378708 A1 Dec. 1, 2022

(30) Foreign Application Priority Data

May 26, 2021 (IN) .............................. 202121023442

(51) Int. Cl.
*A61K 9/20* (2006.01)
(52) U.S. Cl.
CPC .......... *A61K 9/2059* (2013.01); *A61K 9/2068* (2013.01)

(58) Field of Classification Search
CPC ........................... A61K 9/2059; A61K 9/2068
See application file for complete search history.

(56) References Cited

U.S. PATENT DOCUMENTS

| 3,518,344 A | 6/1970 | Tomaich et al. |
| 3,780,186 A * | 12/1973 | Troy ........................ A23L 7/109 426/516 |
| 2005/0079264 A1* | 4/2005 | Leech .................. A61K 9/0056 426/549 |

FOREIGN PATENT DOCUMENTS

| JP | 2002188095 A | 7/2002 |
| JP | 3572547 B2 * | 10/2004 |
| JP | 3572547 B2 | 10/2004 |
| JP | 2008056881 A | 3/2008 |
| WO | 2019013237 A1 | 1/2019 |

* cited by examiner

*Primary Examiner* — Mina Haghighatian
*Assistant Examiner* — Janice Y Silverman

(57) ABSTRACT

A present invention relates to a natural lubricant composition, a tablet comprising a natural lubricant composition and a preparation method thereof. The Natural Lubricant composition for a tablet comprises an active lubricant ingredient selected from a corn flour, a corn starch, and an arrowroot flour. The Natural Lubricant composition for a tablet also comprises a natural oil.

2 Claims, 1 Drawing Sheet

NATURAL LUBRICANT COMPOSITION AND A TABLET

CROSS-REFERENCE TO RELATED APPLICATION(S) AND PRIORITY

The present application does claim priority from the Indian Application No. 202121023442 filed on May 26, 2021.

FIELD OF INVENTION

The present invention relates to the field of a pharmaceutical composition comprising a natural lubricant. More specifically, the present invention relates to a natural lubricant composition and the process of the preparation of the natural lubricant thereof.

BACKGROUND OF INVENTION

Pharmaceutical excipients are generally used in in pharmaceutical formulations as Lubricants, Diluents, Fillers, etc. The Pharmaceutical excipients are also commonly used as food supplements and pharmaceutical formulators. Now-a-days the pharmaceutical industry is inclined towards incorporating more and more natural excipient ingredients in a pharmaceutical formulation. As the natural ingredients are safe, non-allergic and do not cause any severe side effects to the user, the natural ingredient containing natural organic lubricants, diluents or fillers are being developed by the researchers.

Lubricant is one of the necessary excipient in the tableting process of a pharmaceutical formulation. Lubricants are compounds or ingredients which are commonly used to prevent adherence of a tablet to a die wall of a tablet compressing machine or a tablet punching machine. The lubricant excipient enables a compressing machine to easily eject the tablet from a die cavity and also prevent sticking of the tablet to die cavity. A skilled person can understand that without using an appropriate lubricant excipient, tableting of a pharmaceutical formulation or a blend is highly difficult.

Some examples of known lubricants involve Magnesium stearate, Sodium stearyl fumarate, Calcium Stearate, Stearic acid, etc. Such Lubricants are synthetic compounds and may contain impurities such as traces of Mg, Ca, Na. A prolonged administration of impurities in synthetic lubricants may cause a chronic disorder to the body of a user, as each of the pharmaceutical capsule or tablet comprises of at least one of these synthetic lubricant materials.

More specifically, Magnesium Stearate is a vastly used and oldest synthetic lubricant in the pharmaceutical and food domain. This is because, Magnesium stearate shows good lubrication properties, though it causes a little disintegration and dissolution. The Magnesium stearate acts as a lubricant in continuous production of tablet and capsules without sticking, and picking problems to a compressor or a punching machine.

However, recently the consumer's interest in well-being and healthy natural diet has increased and the use of natural additives instead of synthetic additives has seen a gradual increased throughout the pharmaceutical and food industry.

Lubricants are the raw materials which are essentially used while packing, compacting, granulating, compressing and tableting the raw materials in the industrial processes. The lubricants are mainly used by the skilled person to improve the flowability of the raw material powders, increases the filling property of the tablet punching die, reduces friction between punches and facilitates compression of tablets and ejection from the die. It also prevents powder from sticking to the die and punch during compression molding.

Sometimes the food supplementary tablets or herbal ingredient containing tablets are preferred to be made by using only the natural ingredients. In such products also lubricants are necessitated to be incorporated to improve the fluidity of the tablet materials. For these reasons, the synthetic lubricants such as magnesium stearate are inevitably added to the compositions. However, such compositions fail to achieve the overall requirement of using only the natural ingredients because of unavoidable use of synthetic additives.

In state of the art JP-2002188095-A Application discloses about a vegetable oil or fat powder useful as a lubricant or a glidant, and a food composition containing the same. This Application mainly discloses about a composition comprising vegetable oil or fat powder which can be availed by using materials like Lactose, Dextrin, Starch Gum Arabic, etc. acting as lubricant mainly for food supplements tablet. A use of fat powder for formulating a tablet in case of API may not suitable.

In state of the art U.S. Pat. No. 3,518,344-A Application discloses about a main raw material as siloxane polymer (silicone oil family) along with oil and starch solution which is then spray dried on a tablet.

In state of the art JP-3572547-B2 deals with the lubricant containing solid oil and fat powder mix with ingredient which is also a synthetic combination and applicable mostly for food materials.

In state of the art JP-2008056881-A discloses about reduction of mechanical friction using emulsion/suspension of starch water mixture in the tableting process.

Therefore, it remains challenge to develop of a Lubricant composition for pharmaceutical and food supplement tablet comprising only the natural ingredients, which is an alternative to the existing synthetic lubricants and showing comparable or enhanced Lubrication properties to the synthetic lubricants.

Therefore, there is an urgent need to develop an impurity free, economically viable, natural lubricant that is providing better or equivalent effect of lubrication over synthetic lubricants such as Magnesium stearate in a pharmaceutical or food supplement tablet manufacturing process, and which is readily adaptable at the industrial level with ease in scale-up in an economical manner.

OBJECTIVES OF THE INVENTION

The main objective of the present invention is to develop a natural lubricant composition for pharmaceutical formulations such as tablets, capsules and food supplements.

Another objective of the present invention is to provide an alternative for synthetic lubricants such as Magnesium Stearate, without health hazards and compatible for use as an excipient in pharmaceutical as well as food supplement.

Yet another objective of the present invention is to provide a cost effective, economically viable natural lubricant composition.

Still another objective of the present invention is to provide a natural lubricant composition comprising one or more natural organic materials in a predefined ratio.

SUMMARY OF THE INVENTION

Before the present compositions, processes, method, and products are described in the said proposed invention, it is to be understood that the disclosed invention is not limited to the specific compositions, process, methods, and products as described herein, as there can be multiple possible embodiments which are not expressly illustrated in the present invention but may still be practicable within the scope of the invention. It is also to be understood that the terminology used in the description is for the purpose of describing the versions or embodiments only and is not intended to limit the scope of the present application.

The instant invention describes a natural lubricant composition for a tablet comprising an active natural lubricant ingredient and a natural oil as a lubrication enhancer and the process of preparation thereof. The instant invention further describes a tablet comprising the natural lubricant composition and a process of preparation of the tablet.

Accordingly, the present invention provides a natural lubricant composition. The components of the said natural lubricant composition are disclosed hereafter. The said natural lubricant composition may comprise an active lubricant ingredient selected from a corn flour, a corn starch, and an arrowroot flour. The said natural lubricant composition may comprise a natural oil.

In another embodiment of the present invention, a process of preparing a natural lubricant composition comprising various steps is disclosed. The said process is described hereafter. The said process may comprise a step of dry mixing and homogenizing of an active ingredient selected from corn flour, corn starch, and arrowroot with a natural oil.

In yet another embodiment of the present invention, a tablet comprising a natural Lubricant composition for a tablet is disclosed. The said tablet may comprise an active lubricant ingredient selected from corn flour, corn starch, and arrowroot flour; and a natural oil.

In yet another embodiment of the present invention, the natural oil may be selected from at least one of Sunflower oil, and soyabean oil.

In still another embodiment of the present invention, a process of preparing a tablet comprising various steps is disclosed. The said process is described hereafter. The said process may comprise a step of mixing an active pharmaceutical ingredient, and an excipient to prepare mixed powder of a tablet material. The said process may comprise adding to and mixing the mixed powder of the tablet material with the natural lubricant composition. The said process may further comprise milling and compacting (205) the mixed powder to form granules of the tablet material. The said process may further comprise tableting the granules to obtain a tablet comprising a natural lubricant composition.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to refer to features and components.

DETAILED DESCRIPTION OF THE INVENTION

Figure 1:
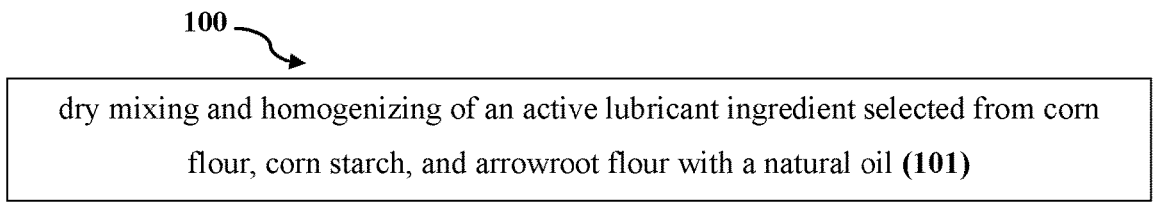
FIG. 1 depicts a process (100) of preparing a natural lubricant composition, in accordance with an embodiment of the present invention.

The words "comprising", "having", "containing", "including" and other forms thereof, are intended to be equivalent in meaning and be open-ended in that an item or items following any one of these words is not meant to be an exhaustive listing of such item or items or meant to be limited to only the listed item or items.

It must also be noted that, the singular forms "a", "an", and "the" include plural references unless the context clearly dictated otherwise, although any methods similar or equivalent to those described herein can be used in the practice or testing of embodiments of the present invention, wherein the exemplary methods are described. The disclosed embodiments are merely exemplary of the disclosure of the present invention, which may be embodied in various forms.

Various modifications to the embodiment may be readily apparent to those skilled in the art and the generic principles herein may be applied to other embodiments. However, one of ordinary skill in the art may readily recognize that the present invention is not intended to be limited to the embodiments illustrated but is to be accorded the widest scope consistent with the principles and the features described herein.

No terminology in this application should be construed as indicating any non-claimed element as essential or critical. The use of any and all examples, or exemplary language (e.g., "such as") provided herein, is intended merely to better illuminate example embodiments and does not pose a limitation on the scope of the claims appended hereto unless otherwise claimed.

Recitation of ranges of values herein is merely intended to serve as a shorthand method of referring individually to each separate value falling within the range, unless otherwise indicated herein, and each separate value is incorporated into the specification as if it were individually recited herein. Where a specific range of values is provided, it is understood that each intervening value, to the tenth of the unit of the lower limit unless the context clearly dictates otherwise, between the upper and lower limit of that range and any other stated or intervening value in that stated range, is included therein. All smaller sub-ranges are also included. The upper and lower limits of these smaller ranges are also included therein, subject to any specifically excluded limit in the stated range.

The present invention is described in detail hereinafter. The present disclosure relates to a natural lubricant composition and a process of preparation of the natural lubricant composition. The present disclosure also related to a tablet comprising a natural lubricant composition and a process of preparing a tablet comprising a natural lubricant composition.

The main purpose of the discloses invention is to employ a calcium (Ca), magnesium (Mg), sodium (Na) trace impurity free, economically viable natural lubricant composition in a tablet manufacturing process. The said natural lubricant composition solves the problem of disintegration and dissolution of the tablets at the step of tablet compression, or tablet punching in the tablet manufacturing process. The said natural lubricant composition particularly reduces the friction between the granules of the tablet material and thereby minimizes the sticking and picking problem in the in the tablet manufacturing process.

The present disclosure mainly describes a natural lubricant composition comprising one or more components. The natural lubricant composition follows a process a process of preparation comprising sequentially designed steps configured by sequential incorporation of one or more components for obtaining the said natural lubricant composition.

In one embodiment of the present invention, a natural lubricant composition is disclosed in accordance with an embodiment of the present invention. The natural lubricant composition may comprise an active lubricant ingredient selected from a natural organic lubricant and a natural oil as a lubricity enhancer.

In another embodiment of the present invention, the natural lubricant composition may comprise an active lubricant ingredient selected from a corn flour, a corn starch, and an arrowroot flour. The natural lubricant composition may further comprise a natural oil. The natural oils is a vegetable oil. The said natural oil may be selected from at least one of but not limited to sunflower oil and soyabean oil.

In a preferred embodiment of the present invention, the natural lubricant composition may comprise an active lubricant ingredient as a corn flour and a natural oil is selected as sunflower oil.

In some embodiments of the present invention, the natural lubricant composition may also be incorporated in combination with the synthetic lubricants such as but not limited to magnesium stearate, Calcium Stearate, Sodium Stearyl Fumarate and Stearic acid in one or more tablet manufacturing processes.

In another embodiment of the present invention, wherein a weight percentage of the active lubricant ingredient is 95-99.5% based on the total weight of the natural lubricant composition.

In another embodiment of the present invention, wherein a weight % of the natural oil is 0.5-5% based on the total weight of the natural lubricant composition.

In a preferred embodiment of the present invention wherein the weight percentage ratio of the natural oil in the natural lubricant composition with the natural organic lubricant is between 99.9:0.01 to 90.1:9.99, preferably between 99:1 to 94.1:6.99, and most preferably 98:2 respectively.

In yet another embodiment of the present invention wherein, a process of preparing a natural lubricant composition is illustrated in accordance with an embodiment of the present invention. The process may involve one or more equipment selected from a shaker, mixer, blender, and milling machine. The process may involve one or more components selected as an active lubricant ingredient and a natural oil in accordance with an embodiment of the present invention.

In one embodiment of the present invention wherein, FIG. 1 depicts a process (100) of preparing a natural lubricant composition.

Referring to FIG. 1, a process (100) of preparing a natural lubricant composition is illustrated in accordance with an embodiment of the present invention. The said process may comprise a step of dry mixing and homogenizing (101) of an active lubricant ingredient selected from corn flour, corn starch, and arrowroot flour with a natural oil.

In another embodiment of the present invention, a tablet comprising a natural lubricant composition is disclosed in accordance with an embodiment of the present invention. The tablet may comprise a natural lubricant composition comprising an active lubricant ingredient selected from a natural lubricant composition and a natural oil as a lubricity enhancer.

In yet another embodiment of the present invention, wherein the weight percentage of the natural lubricant composition is 0.5-5% based on the total weight of the tablet. In a preferred embodiment of the present invention, the tablet comprising the natural lubricant composition may comprise an active lubricant ingredient as a corn flour and a natural oil is selected as sunflower oil. As the overall content of the natural lubricant composition is very less i.e., at max 5%, a storage stability of the tablet may remain intact and does not get affected by the incorporation of the natural lubricant composition.

Figure 2:
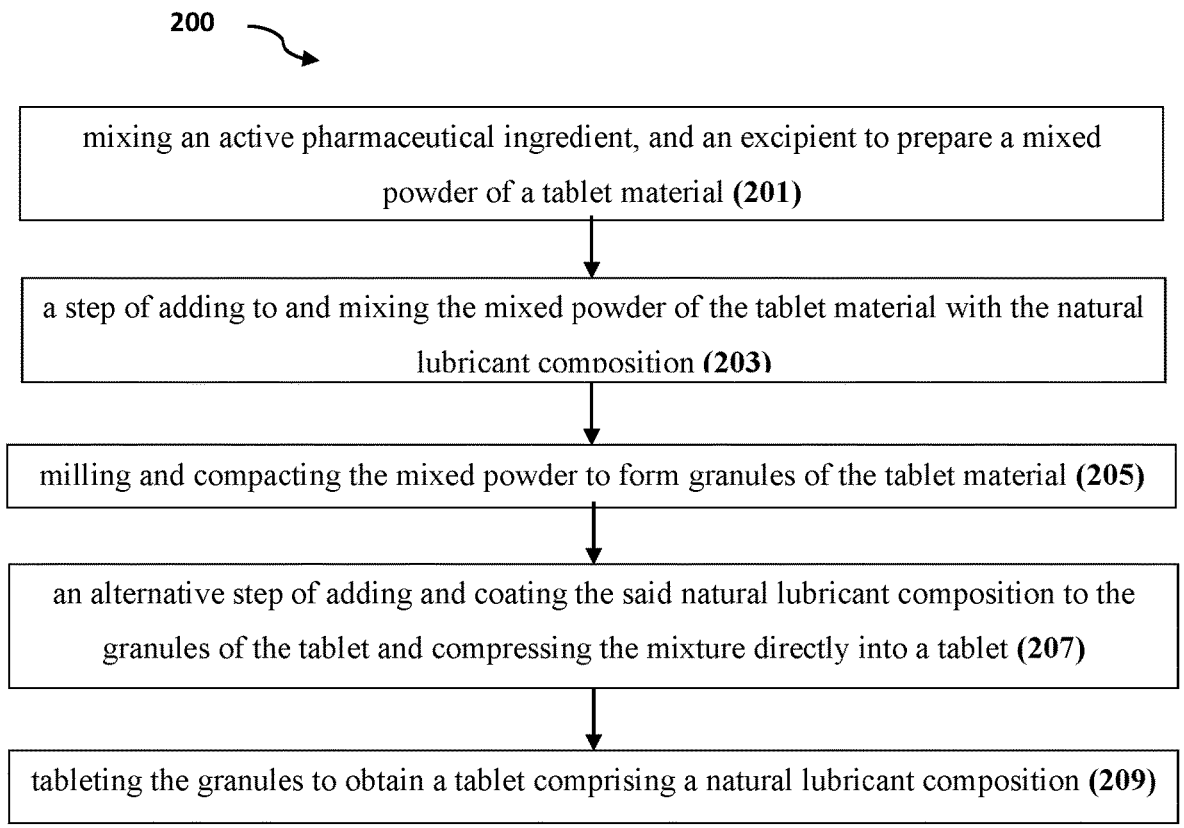
FIG. 2 depicts a process (200) of preparing a tablet comprising a natural lubricant composition, in accordance with an embodiment of the present invention.

In one embodiment of the present invention wherein, FIG. 2 depicts a process (200) a tablet comprising a natural lubricant composition.

Referring to FIG. 2, a process (200) of preparing a tablet comprising a natural lubricant composition is illustrated in accordance with an embodiment of the present invention. The said process may comprise a step of mixing (201) an active pharmaceutical ingredient, and an excipient to prepare a mixed powder of a tablet material. The said process may further comprise a step of adding (203) to and mixing the mixed powder of the tablet material with the natural lubricant composition in accordance with an embodiment of the present disclosure. The said process may further comprise a step of milling and compacting (205) the mixed powder to form granules of the tablet material. The said process may further comprise a step of tableting (209) the granules to obtain a tablet comprising a natural lubricant composition.

In one embodiment of the present invention, wherein the step of adding (203) to and mixing the mixed powder of the tablet material with the natural lubricant composition may be replaced with an alternative step of adding and coating (207) the said natural lubricant composition to the granules of the tablet and compressing the mixture directly into a tablet.

In one embodiment the step of adding and coating (207) the said natural lubricant composition to the granules of the tablet involves coating the granules of the tablet material with a thin layer of the natural lubricant composition. The coating of the natural lubricant composition enhances flowability of the granules of the tablet material and reduces the friction between the granules at the step of compressing or punching the tablet.

In one embodiment of the present invention, the natural lubricant composition may be used in a direct compression of the tableting material after the mixing of a pharmaceutically active ingredient and excipients to obtain a pharmaceutical tablet and/or a food supplement tablet.

In one exemplary embodiment of the present invention, in the granules or powder of tableting material, the said natural lubricant composition is blended for a predetermined time already validated as per standards. In this predefined time each and every granule of the tableting material may get thinly coated (a coating layer is in few nanometer) with the said natural lubricant composition. The coating of the natural lubricant composition is configured to decrease friction among granules of the tableting material and improves the ease of punching process by reducing the sticking picking of the tableting material to the punching die.

In accordance with an embodiment of the present invention, the tablet may be of any dosage quantity selected as but not limited to 1 mg, 5 mg, 10 mg, 50 mg, 100 mg, 200 mg, 500 mg, etc.

As used herein, the term "tablet" means a tablet prepared from pharmacologically useful raw materials by only a physical process without carrying out a chemical extraction process or a chemical reaction.

In the present invention, the tablet may be defined as be any tablet of food, feed, health functional food or pharmaceutical. The tablet may be prepared by a conventional tablet manufacturing method known in the art, and the ingredients may include an active ingredient, a binder, an excipient, a disintegrant, and a lubricant.

In the present invention, the natural lubricant composition may be used in but not limited to a tablet or powder for food, feed, health functional food, pet food or pharmaceutical.

According to the present invention, the natural lubricant composition of the present invention not only improves the flowability or slippage of the powder, but also reduces the friction between the powders and the friction with the tableting punch or die at the time of tableting, which is similar to that of the synthetic lubricant. As it shows the efficacy as a lubricant, it can be usefully utilized as a natural lubricant that is harmless to the human body.

The instant invention is further described by the following examples:

Experimental Details

After performing various experiments, a significant result could be seen in the characteristic properties of the said natural lubricant composition. The natural lubricant composition as described above and further in the consequent examples showed better performance in lubrication properties and controlled disintegration and dissolution of the tablets comprising the natural lubricant composition.

Various laboratory tests such as Angle of repose and Lubrication index were conducted for the natural lubricant composition.

In one of the implementation of the present invention, wherein several factors were studied, which may associate with the suitability of the natural ingredients as a compatible lubricants in the tablet manufacturing process with respect to the existing synthetic lubricants.

The number of experiments of the said natural lubricant in accordance with the embodiments of the invention comprising a natural organic lubricant selected from corn flour, corn starch and arrowroot in combination with or without the natural oils selected from vegetable oils such as sunflower oil and soyabean oil were conducted. Surprisingly, the combination of the natural organic lubricant selected as corn flour and the natural oil selected as sunflower oil showed the comparable/superior lubrication properties without losing the aesthetic outlook of the tablet. The detailed experimental data is further represented in the examples below.

Example 1: Preparation Method a Natural Lubricant Composition and Test Data

The experiment was carried out to select an alternative natural lubricant showing enhanced efficacy in view of synthetic Magnesium Stearate used as a lubricant in pharmaceutical tablet manufacturing process. Firstly, the lubricating properties of various identified natural lubricants namely corn flour (hereinafter may be alternatively referred to as "Cf"), Corn starch (hereinafter may be alternatively referred to as "Cs"), Arrowroot (hereinafter may be alternatively referred to as "A"), Wheat flour (hereinafter may be alternatively referred to as "Wf").

Furthermore, to represent the effective lubricating properties of the said natural lubricant composition, a data of weight percentage content of natural lubricant composition were then compared with the predefined weight percentage Magnesium Stearate in weight percentage Reference grains data.

In process of making a tablet, an active pharmaceutical ingredient (API) either in granular or powder form is mixed with excipients like diluents, glidants to form a tablet material (may also be interchangeably referred to as "reference grain). The said tablet material is then either granulated with the wet/dry process and then blended or coated with the natural lubricant composition in accordance with the embodiment of the present invention in a blender & then taken for punching tablet or filling capsules.

In the below table, the reference grain data is the overall tableting material which is to be blended with or coated by the lubricant in particular proportion for manufacturing a pharmaceutical or food supplementary tablet. The reference grain component may optionally comprise an active pharmaceutical ingredient, and excipients like a glidant, a binder, diluents etc.

To measure the lubricity of the natural lubricant composition of the present invention and the synthetic lubricants the two main lubrication indices were determined namely Angle of repose and Lubrication index.

The Angle of repose and Lubrication index are the functions of flow ability i.e., the criteria of the sliding ability of one particle over another particle in a fine powder mix. Therefore, the optimum values of the Angle of repose and Lubrication index indicate the lubricity of the lubricant.

In the pharmaceutical industry, following criterial of the Angle of repose is used to determine the flow character of the particle and thereby a lubricity of the lubricant in the mix.

| Angle of repose | flow character |
|---|---|
| 25-30 | Excellent |
| 31-35 | Good |
| 36-40 | Fair |

Angle of repose can be defined as the maximum angle possible between surface of pile of powder and horizontal plane. It is characteristic related to inter particulate friction or resistance movement between particles.

Referring to Table 1, the lubricating properties data showing Angle of repose and Lubrication index for a predefined % Magnesium Stearate in % Reference grains was then determined as shown in Table 1 below.

TABLE 1

| Sr. No. | % Reference grains-1 | Magnesium Stearate | Angle of Repose | Lubrication Index |
|---|---|---|---|---|
| 1. | 100% | 0% | 33.83° | — |
| 2. | 99% | 1% | 32.82° | 298 |
| 3. | 98% | 2% | 32.77° | 313 |
| 4. | 97% | 3% | 32.68° | 340 |
| 5. | 96% | 4% | 32.64° | 352 |
| 6. | 95% | 5% | 32.55° | 378 |

Further, Lubricating properties such as Angle of repose and Lubrication index of each of the predefined % natural lubricants were measured with % Reference grains.

Table 2 represents the lubricating properties data showing Angle of repose and Lubrication index for a predefined % Corn starch (Cs) in % Reference grains.

TABLE 2

| Sr. No. | % Reference grains-1 | % Natural Organic Lubricant- (Cs) | Angle of Repose | Lubrication Index |
|---|---|---|---|---|
| 1. | 100% | 0% | 32° | — |
| 2. | 99% | 1% | 31.09° | 284 |
| 3. | 98% | 2% | 30.46° | 481 |

TABLE 3

Table 3 represents the lubricating properties data showing Angle of repose and Lubrication index for a predefined % Arrowroot (A) in % Reference grains.

| Sr. No. | % Reference grains-1 | % Natural Organic Lubricant- (A) | Angle of Repose | Lubrication Index |
|---|---|---|---|---|
| 1. | 100% | 0% | 32° | — |
| 2. | 99% | 1% | 31.21° | 246 |
| 3. | 98% | 2% | 30.66° | 418 |

TABLE 4

Table 4 represents the lubricating properties data showing Angle of repose and Lubrication index for a predefined % Wheat flour (Wf) in % Reference grains.

| Sr. No. | % Reference grains-1 | % Natural Organic Lubricant- (Wf) | Angle of Repose | Lubrication Index |
|---|---|---|---|---|
| 1. | 100% | 0% | 32° | — |
| 2. | 99% | 1% | 31.84° | 50 |
| 3. | 98% | 2% | 30.96° | 321 |

TABLE 5

| Sr. No. | % Reference grains-1 | % Natural Organic Lubricant- (Cf) | Angle of Repose | Lubrication Index |
|---|---|---|---|---|
| 1. | 100% | 0% | 32° | — |
| 2. | 99% | 1% | 31.116° | 276 |
| 3. | 98% | 2% | 30.60° | 437 |

In one implementation of the present disclosure, an existing technology for manufacturing synthetic lubricants such as Magnesium stearate is a wet process or dry process involving a chemical reaction and modification done with magnesium hydroxide & stearic acid. There are higher chances of involving certain impurities which may be harmful to the health and well-being of the consumer. Therefore, the said natural lubricant composition is derived to be used as a definite alternative to the synthetic lubricants.

It was observed that the Organic Natural Lubricants selected as Cs, A, Cf, and Wf showed comparative lubricating properties with respect to a Synthetic Lubricant Magnesium Stearate.

Example 2

After determining good results in view of Lubricating properties, additional Experimentation was carried out to select a Lubrication enhancing Natural oil component. In this study, the Natural Organic Lubricants were selected as Cs, A, Cf, and Wf were blended with the Natural oils selected as Sunflower oil (hereinafter may be alternatively referred to as Sf-oil), and Soyabean oil (hereinafter may be alternatively referred to as S-oil). The Natural Organic Lubricants and Lubrication enhancer Natural oils were then blended together to obtain a synergistic composition of Natural Lubricant in different predefined proportions. The Natural Lubricant composition then mixed with % Reference grain-1 as shown in Table 6-11.

The % ratio of % Reference grain-1, % Natural organic lubricant and % Natural oil was varied in such a way that the % Natural organic lubricant is 1% and the % Reference grain-1 is 99% and the % Natural oil was added between 0.5-5% of overall combination of the blend.

Table 6 represents the lubricating properties data showing Angle of repose and Lubrication index for a predefined % (1% Arrowroot Flour (A)+99% Reference grains) mixed with predefined % of Natural oil-1 i.e., Soyabean oil.

TABLE 6

| Sr. No. | Mixed (Reference grains 1-99% + A-1%) | Natural oil-1 | Angle of Repose | Lubrication Index | Remarks |
|---|---|---|---|---|---|
| 1. | Reference grains-1-100% | — | 35.05° | — | |
| 2. | 99.5% | 0.5% | 34.28° | 219 | Colour is yellow |
| 3. | 99% | 1% | 33.78° | 362 | |
| 4. | 98% | 2% | 33.40° | 470 | |
| 5. | 97% | 3% | 33.40° | 470 | |
| 6. | 96% | 4% | 33.40° | 470 | |
| 7. | 95% | 5% | 33.69° | 388 | |

Table 7 represents the lubricating properties data showing Angle of repose and Lubrication index for a predefined % (1% Corn Flour (Cf)+99% Reference grains) mixed with predefined % of Natural oil-1 i.e., Soyabean oil.

TABLE 7

| Sr. No. | Mixed (Reference grains 1-99% + Cf-1%) | Natural oil-1 | Angle of Repose | Lubrication Index | Remarks |
|---|---|---|---|---|---|
| 1. | Reference grains-1-100% | — | 35.05° | — | |
| 2. | 99.5% | 0.5% | 33.54° | 430 | Colour is yellow |
| 3. | 99% | 1% | 33.11° | 553 | |
| 4. | 98% | 2% | 32.83° | 633 | |
| 5. | 97% | 3% | 32.55° | 760 | |
| 6. | 96% | 4% | 32.41° | 760 | |
| 7. | 95% | 5% | 32.27° | 838 | |

Table 8 represents the lubricating properties data showing Angle of repose and Lubrication index for a predefined % (1% Corn starch (Cs)+99% Reference grains) mixed with predefined % of Natural oil-1 i.e., Soyabean oil.

TABLE 8

| Sr. No. | Mixed (Reference grains 1-99% + Cs-1%) | Natural oil-1 | Angle of Repose | Lubrication Index | Remarks |
|---|---|---|---|---|---|
| 1. | Reference grains-1-100% | — | 35.05° | — | |
| 2. | 99.5% | 0.5% | 33.40° | 470 | Colour is dark yellow |
| 3. | 99% | 1% | 32.96° | 596 | |
| 4. | 98% | 2% | 32.27° | 793 | |
| 5. | 97% | 3% | 32° | 870 | |
| 6. | 96% | 4% | 32° | 870 | |
| 7. | 95% | 5% | 32° | 870 | |

Table 9 represents the lubricating properties data showing Angle of repose and Lubrication index for a predefined % (1% Arrowroot (A)+99% Reference grains) mixed with predefined % of Natural oil-2 i.e., Sunflower oil.

TABLE 9

| Sr. No. | Mixed (Reference grains 1-99% + A-1%) | Natural oil-2 | Angle of Repose | Lubrication Index | Remarks |
|---|---|---|---|---|---|
| 1. | Reference grains-1-100% | — | 35.05° | — | |
| 2. | 99.5% | 0.5% | 33.98° | 305 | Colour is white |
| 3. | 99% | 1% | 33.83° | 348 | |
| 4. | 98% | 2% | 33.39° | 473 | |
| 5. | 97% | 3% | 33.11° | 553 | |
| 6. | 96% | 4% | 32.82° | 636 | |
| 7. | 95% | 5% | 32.82° | 636 | |

Table 10 represents the lubricating properties data showing Angle of repose and Lubrication index for a predefined % (1% Corn flour (Cf)+99% Reference grains) mixed with predefined % of Natural oil-2 i.e., Sunflower oil.

TABLE 10

| Sr. No. | Mixed (Reference grains 1-99% + Cf-1%) | Natural oil-2 | Angle of Repose | Lubrication Index | Remarks |
|---|---|---|---|---|---|
| 1. | Reference grains-1-100% | — | 35.05° | — | |
| 2. | 99.5% | 0.5% | 34.28° | 220 | Colour is white after mixing oil |
| 3. | 99% | 1% | 33.83° | 342 | |
| 4. | 98% | 2% | 33.83° | 348 | |
| 5. | 97% | 3% | 33.68° | 390 | |
| 6. | 96% | 4% | 33.25° | 513 | |
| 7. | 95% | 5% | 32.55° | 713 | |

Table 11 represents the lubricating properties data showing Angle of repose and Lubrication index for a predefined % (1% Corn starch (Cs)+99% Reference grains) mixed with predefined % of Natural oil-2 i.e., Sunflower oil.

TABLE 11

| Sr. No. | Mixed (Reference grains 1-99% + Cf-1%) | Natural oil-2 | Angle of Repose | Lubrication Index | Remarks |
|---|---|---|---|---|---|
| 1. | Reference grains-1-100% | — | 35.05° | — | |
| 2. | 99.5% | 0.5% | 33.69° | 388 | Colour is dark yellow |
| 3. | 99% | 1% | 33.39° | 473 | |
| 4. | 98% | 2% | 33.30° | 499 | |
| 5. | 97% | 3% | 33.28° | 505 | |
| 6. | 96% | 4% | 33.25° | 513 | |
| 7. | 95% | 5% | 33.11° | 553 | |

In this study of the Example 3, the synergistic combination of Corn Flour and Sunflower oil was determined as better a Natural lubricant composition showing the enhanced and comparable lubricating properties in view of Angle of repose and Lubrication index.

Example 3

In the Example 3, a process of developing Natural lubricant composition is disclosed. In the first step, dry mixing of a Natural organic lubricant ingredient and a Natural organic oil in predefined proportions was carried out to obtain a Natural lubricant composition. In the next step, a synergistic blend of Natural lubricant composition was processed to obtain a white lubricant powder for use in tablet making process.

In this example, a combination of the natural organic lubricant selected as corn flour powder and sunflower oil as a natural organic oil were blended together by a dry mixing process to obtain the Natural lubricant composition. The resulting Natural lubricant composition is determined as good for human health and can be categorized as a clean label lubricant. In one embodiment, a clean label lubricant means making a product by using as few ingredients in a predetermined proportion and making sure those ingredients are items that consumers recognize and regard as wholesome.

In one implementation, a typical process of dry mixing was carried out, in which a predefined amount of dried corn flour was added to the mixer unit and further the predetermined amount of sunflower oil was added by slow addition method. The process of mixing was continued for a specific period of time to make the product homogeneous to obtain the Natural lubricant composition. The Natural lubricant composition comprising a predetermined amount of corn flour and sunflower oil is then used for making tablets. The as prepared Natural lubricant composition was observed to be providing a good lubrication while making the pharmaceutical or a food supplement tablet and also provides good shining, and smooth surfaces to pharmaceutical or food supplement tablets.

Table 12 discloses about a comparative data of the Natural lubricant composition comprising a predetermined amount of corn flour and sunflower oil with the existing synthetic Lubricants used while manufacturing of pharmaceutical tablets. showing the angle of repose and Lubrication index.

TABLE 12

| Sr. No. | Reference grains | Lubricant used | % of Lubricant used | Angle of repose(°) | Lubrication Index |
|---|---|---|---|---|---|
| 1 | 100% | — | 0% | 36.19 | — |
| 2 | 99% | Magnesium Stearate | 1% | 34.74 | 400 |
| 3 | 98% | Magnesium Stearate | 2% | 34.43 | 478 |
| 4 | 99% | Calcium Stearate | 1% | 35.69 | 138 |
| 5 | 98% | Calcium Stearate | 2% | 35.53 | 182 |
| 6 | 99% | Sodium Stearyl Fumarate | 1% | 34.43 | 478 |
| 7 | 98% | Sodium Stearyl Fumarate | 2% | 34.23 | 528 |
| 8 | 99% | Stearic acid | 1% | 36.02 | 47 |
| 9 | 98% | Stearic acid | 2% | | |
| 10 | 99% | Natural organic Lubricant | 1% | 35.37 | 229 |
| 11 | 98% | Natural organic Lubricant | 2% | 34.43 | 486 |

Therefore, the data represented in the Table 12 shows that Lubrication index the Natural Lubricant composition as prepared by the abovementioned process and comprising a predefined amount of Corn flour and sunflower oil, shows comparable results as Magnesium Stearate and better properties of angle of repose and lubrication index than Calcium Stearate & Stearic acid, whereas it is slightly lower compared to Sodium stearyl fumarate. The Natural Lubricant composition comprising a natural organic Lubricant and a natural organic oil in a predefined proportion as disclosed in Example 2 and 3 resulted as a good alternative to the existing synthetic lubricants such as Magnesium Stearate.

Example 4

In this Example disintegration time of the tablet comprising the Natural lubricant composition of present disclosure was compared with the three samples of the tablet comprising the synthetic lubricant i.e., Magnesium stearate. The experimental finding are represented in the Table 13 below. The disintegration was performed in a triplicate on a 500 mg tablet comprising the 10 mg of the lubricant ingredient selected from Magnesium stearate and Natural Lubricant composition as prepared by the abovementioned process and comprising corn flour and sunflower oil.

TABLE 13

| Sr No | Magnesium stearate Disintegration time | Natural lubricant composition Disintegration time |
|---|---|---|
| 1 | 15 min | 14 min |
| 2 | 15.5 min | 14 min |
| 3 | 14 min | 13.5 min |

Referring to the Table 13 it can be observed that the disintegration time of the natural lubricant composition is comparable or lesser than that of the synthetic lubricant i.e., Magnesium stearate.

The said Natural Lubricant composition comprising a natural organic lubricant and a natural organic oil as described in the present invention may comprise the following advantages:

The Natural Lubricant composition disclosed in the instant invention is safe, and cost-effective and can be used in pharmaceutical tablet manufacturing as an effective lubricant.

The said Natural Lubricant composition may also be used as a Lubricant in food supplements, and Veterinary Food.

The Natural Lubricant composition disclosed in the instant invention effectively controls the disintegration & dissolution of tablet in the tablet compression and tablet punching process.

The Natural Lubricant composition disclosed in the instant invention effectively controls the sticking and picking problems of the pharmaceutical tablet occurring at the step of tablet punching.

A pharmaceutical or food supplement tablet manufactured by incorporating the Natural Lubricant composition disclosed in the instant invention retains a white color, good shine, and smooth surfaces to the tablets.

The Natural Lubricant composition of the present invention involves natural materials, which are safe to the consumer, does not contain impurities such as Na, Mg, Ca traces, easily reproducible and thereby making it more economical, and industrially & commercially viable.

This natural lubricant composition of the present invention may prevent a sticking phenomenon from occurring in direct compression.

According to the present invention, the flowability of a tableting material comprising a natural lubricant composition of the present invention may also be improved.

The embodiments, examples, and alternatives of the preceding paragraphs or the description and drawings, including any of their various aspects or respective individual features, may be taken independently or in any combination thereof. Features described in connection with one embodiment apply to all embodiments, unless such features are incompatible.

The invention claimed is:

1. A natural lubricant composition for a tablet consisting essentially of:
   an active lubricant ingredient, wherein the active lubricant ingredient is corn flour, and wherein the active lubricant ingredient is present at 95-99.5% by weight based on the total weight of the composition; and
   a natural oil selected from at least one of sunflower oil, and soyabean oil, wherein the natural oil is present at 0.5-5% by weight based on the total weight of the natural lubricant composition.

2. The natural lubricant composition as claimed in claim 1, wherein the natural oil is sunflower oil.

* * * * *